United States Patent [19]
Chen et al.

[11] Patent Number: 5,888,787
[45] Date of Patent: Mar. 30, 1999

[54] SELECTIVE ENZYMATIC OXIDATION OF AROMATIC METHYL GROUPS TO ALDEHYDES BY OXYGEN IN THE PRESENCE OF A LACCASE-MEDIATOR CATALYST

[75] Inventors: Chen-Loung Chen, Raleigh; Josef S. Gratzl, Cary; Adrianna G. Kirkman, Raleigh, all of N.C.; Antje Potthast, Floha; Thomas Rosenau, Eisenach, both of Germany

[73] Assignee: North Carolina State University, Raleigh, N.C.

[21] Appl. No.: 677,338

[22] Filed: Jul. 2, 1996

[51] Int. Cl.$^6$ .............................. C12P 7/24; C12N 9/02; C12N 1/14; C07C 45/00

[52] U.S. Cl. ................ 435/147; 435/189; 435/254.1; 568/426; 568/431

[58] Field of Search ........................ 435/147, 189, 435/254.1; 568/425, 426, 431

[56] References Cited

FOREIGN PATENT DOCUMENTS

92/20857  11/1992  WIPO .

OTHER PUBLICATIONS

Robertson et al. Oxidation of nitrotoluenes by toluene dioxygenase: Evidence for a monooxygenase reaction, Appl. Environ. Microbiol. (1992) 58(8): 2643–48, Aug. 1992.

Morrison et al. *Organic Chemistry*, Second Edition, pp. 386 and 619 (Jul., 1967) (Allyn & Bacon, Inc. ; Boston.

Mijs et al. *Organic Synthesis by Oxidation With Metal Compunds*, pp. 1–883 (1986), (Plenum Press; New York).

Barton et al. *Tetrahedron Letters*, "Preparation of Aldehydes and Ketones by Oxidation of Benzylic Hydrocarbons with Benzeneseleninic Anhydride", No. 35, pp. 3331–3334 (1979).

Nishimura *Organic Synthesis*, "Methods of Preparation", vol. 4, pp. 713–715 (1963).

Morohoshi et al. *Mokuzai Gakkaishi*, "Degradation of Lignin by the Extracellular Enzymes of *Coriolus versicolor* IV", vol. 33, No. 3, pp. 218–225 (1987).

Rosenau et al. *Synthetic Communications*, "A Mild, Simple and General Procedure for the Oxidation of Benzyl Alcohols to Benzaldehydes", No. 2, pp. 315–320 (Feb. 1996) vol. 26.

Solomon et al. *Chem. Rev.*, "Electronic Structures of Active Sites in Copper Proteins: Contributions to Reactivity", vol. 92, pp. 521–542 (1992).

Solomon et al. *Science*, "Electronic Structure Contributions to Function in Bioinorganic Chemistry", vol. 259, pp. 1575–1581 (Mar. 1993).

Bourbonnais et al. *Federation of European Biochemical Letters*, "Oxidation of Non–Phenolic Substrates", vol. 267, No. 1, pp. 99–102, (Jul. 1990).

Wong et al. *Angew. Chem. Int. Ed. Engl.*, "Enzymes in Organic Synthesis: Application to the Problems of Carbohydrate Recognition (Part 1)", vol. 34, pp. 412–432 (1995).

Paice et al. *Applied and Evnironment Microbiology*, "Manganese Peroxidase, Produced by Trametes versicolor during Pulp Bleaching, Demethylates and Delignifies Kraft Pulp", vol. 59, No. 1, pp. 260–265 (Jan. 1993).

Agematu et al. *Biosci. Biotech. Biochem.*, "Oxidative Decarboxylations of 4–Hydroxymandelic Acid and 2–(4–Hydroxyphenyl) glycine by laccase from *Coriolus versicolor* and Bilirubin Oxidase from *Trachyderma tsunodae* and *Myrothecium verrucaria*", vol. 57, No. 11, pp. 1877–1881. (1993).

Potthast et al. "Selective enzymatic oxidation of aromatic groups to aldehydes," J. Org. Chem. Jul. 14, 1995 60:4320–1.

Potthast et al. "A novel method for the conversion of benzyl alcohols to benzaldehydes by laccase–catalyzed oxidation," J. Molec. Catalysis A: Chemical (1996): 5–9, 1996.

Bourbonnais et al. "Demethylation and delignification of kraft pulp by Trametes versicolor laccase in the presence of 2,2'–azinobis–(3–ehtylbenzthiazoline–6–sulphonate," Appl. Bicrobiol. Biotechnol. (1992): 36:823–7.

*Primary Examiner*—Jon P. Weber
*Assistant Examiner*—Susan Hanley
*Attorney, Agent, or Firm*—Jenkins & Wilson, P.A.

[57] ABSTRACT

A method for oxidation of a pendant methyl moiety on an aromatic ring to the pendant aldehyde moiety is presented. The reaction employs laccase and the diammonium salt of 2,2'-azinobis(3-ethylbenzothiazoline-6-sulfonic acid), and is carried out in the presence of oxygen.

9 Claims, No Drawings

SELECTIVE ENZYMATIC OXIDATION OF AROMATIC METHYL GROUPS TO ALDEHYDES BY OXYGEN IN THE PRESENCE OF A LACCASE-MEDIATOR CATALYST

GOVERNMENT INTEREST

The United States Government has an interest in the subject patent application, as research funds were provided through the United States Department of Agriculture under Grant No. 95-37103-2268.

TECHNICAL FIELD

The present invention relates, in general, to a method of catalytic conversion of selected aromatic compounds so that a moiety pendent on the compound becomes an aldehyde moiety. More particularly, the present invention relates to a method for oxidizing a pendent methyl moiety of an aromatic compound, in the presence of a suitable enzymatic catalyst and a suitable mediator, to convert the compound into the corresponding aromatic aldehyde.

BACKGROUND OF THE INVENTION

Procedures in organic syntheses frequently employ a step in which a alkyl moiety that is pendent on an aromatic ring is oxidized. Typically, the alkyl moiety is oxidized to the corresponding carboxylic acid moiety or alcohol moiety. However, when the alkyl moiety is methyl, attempts at selective oxidation to convert the methyl moiety into something other than the corresponding carboxylic acid moiety or hydroxymethyl moiety have been extremely difficult.

For instance, it is well known to those skilled in the art that the methyl moiety in toluene can be selectively oxidized in order to convert the toluene into benzaldehyde using a lengthy 2-step procedure that requires formation of an intermediate. First, the methyl moiety is chlorinated with heat (i.e., chlorine gas is bubbled into boiling toluene) to form benzal chloride as the intermediate. This first step is followed by hydrolysis at an elevated temperature to remove the 2 chlorines from the dichloromethyl moiety and result in the formation of HCl and benzaldehyde. See, Morrison and Boyd, *Organic Chemistry*, 2d Ed., p. 386 and p. 619 (1966).

Additionally, as reported by Mijs et al. in *Organic Synthesis by Oxidation with Metal Compounds* (1986), transition metal oxidants have been used to attack the pendent methyl moiety in toluene. Nevertheless, the reaction is difficult to stop at the benzaldehyde stage and readily produces a high yield of benzoic acid.

To stop the benzaldehyde from further oxidizing to the corresponding benzoic acid, two main procedures are employed instead of the transition metal oxidant treatment.

In the first procedure, benzeneseleninic acid is employed to achieve selective oxidation of toluene to benzaldehyde, as reported by Barton et al. in "Preparation of Aldehydes and Ketones by Oxidation of Benzylic Hydrocarbons with Benzeneseleninic Anhydride", Vol. 35, *Tetrahedron Letters*, pp. 3331–3334 (1979). However, not only are yields poor, but also reaction times are long.

The second procedure employs glacial acetic acid or acetic anhydride to trap p-nitrobenzaldehyde as p-nitrobenzylidene diacetate, and then, the trapped intermediate is converted to p-nitrobenzaldehyde using chromic acid and chromyl acetate as oxidants (the procedure is substantially similar for the o-isomer), as reported by Nishimura, in Vol. 4, *Organic Synthesis*, pp. 713–715 (1963).

As is well known, aromatic aldehydes and substituted aromatic aldehydes are commercially important. For instance, benzaldehyde is used in the manufacture of dyes, in perfumery, and as a solvent, and nitrobenzaldehyde (a substituted benzaldehyde) is useful as a reagent for isopropyl alcohol and acetone.

Thus, it is desirable to find a way, unlike the above-described procedures, to achieve selective oxidation of toluene (or other aromatics having a pendent methyl moiety) into benzaldehyde (or other respective corresponding aromatics having a pendent aldehyde moiety) not only that can be carried out relatively quickly under relatively mild conditions but also that can achieve high yields of the resultant aldehyde.

SUMMARY AND OBJECTS OF THE INVENTION

Therefore, the present invention provides a method for manufacturing an aromatic aldehyde compound. The method comprises providing (i) an aromatic compound for catalytic conversion into the aromatic aldehyde compound, (ii) an enzymatic catalyst, and (iii) a mediator. The aromatic compound has a pendent methyl moiety on at least one carbon of the aromatic compound and also has at least one unsubstituted position ortho to the carbon having the pendent methyl moiety. For each mol of the aromatic compound that is present, there are present about 5 to 11 mmol of the mediator and a sufficient amount of the catalyst to provide about 25 to 210 Units of enzymatic activity.

The aromatic compound, the enzymatic catalyst, and the mediator are reacted in the presence of oxygen at a temperature from about 20° C. to about 40° C. and a pressure from about 740 mm to about 780 mm and a pH from about 4.0 to about 6.0; and the aromatic aldehyde is obtained from the reaction.

Hence, it is an object of the invention to achieve selective oxidation of aromatics having a pendent methyl moiety into respective corresponding aromatics having a pendent aldehyde moiety, substantially absent the typical production of the corresponding aromatics having a pendent carboxylic acid moiety or hydroxymethyl moiety, as is common in the prior art.

An object of the invention having been stated above, other objects will become evident as the description proceeds, when taken in connection with the accompanying Laboratory Examples as best described below.

DETAILED DESCRIPTION OF THE INVENTION

Selective oxidation of a methyl moiety pendant on an aromatic ring to the corresponding pendent aldehyde has been achieved by reacting an aromatic compound having a pendent methyl moiety, in the presence of a mediator and a suitable enzymatic catalyst. For each mol of the starting material of aromatic compound having a pendent methyl moiety, there should be present about 5 to 11 mmol of the mediator and a sufficient amount of catalyst to provide about 25 to 210 Units of enzymatic activity.

The reaction is to be carried out in the presence of oxygen, and may be carried out in the ambient air, as oxygen is present in the ambient air. However, it is preferred to carry out the reaction with intermittent flushing with pure oxygen, as described in more detail in the Laboratory Examples below.

With regard to the starting material of an aromatic compound having a pendent methyl moiety, this starting material must have an aromatic ring that has at least one pendent methyl moiety on a carbon in the ring. There may be present more than one such methyl-substituted aromatic ring in the starting material compound, but there must be at least one.

By the term aromatic ring, as it is employed here in connection with the methyl-substituted aromatic ring, it is intended to mean that the ring has some degree of unsaturation. Thus, it is intended to include compounds such as 1-methylcyclohexene, as well as compounds such as toluene, as suitable starting materials.

Also, the methyl-substituted aromatic ring must have at least one unsubstituted position of the two positions ortho to carbon having the pendent methyl moiety. While it is not intended to be bound to any theory, it is believed that if each ortho position were substituted with a pendent moiety, then the steric hindrance close to the pendent methyl moiety would be too great for the reaction to proceed.

Preferably, the methyl-substituted aromatic ring is a 5-member or 6-member ring, but it is intended that methyl-substituted compounds with larger aromatic rings, for instance, compounds with 7-member rings such as

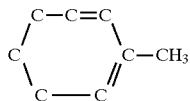

are also included within the method of the present invention.

The methyl-substituted aromatic ring does not necessarily have to be a homocyclic ring of carbon members, and thus, may be heterocyclic and contain one or more sulfur, oxygen, or nitrogen members. For instance, p-methylpyran is a suitable methyl-substituted starting material compound. Moreover, it has been found that the method of the present invention is particularly suitable for 5-member heterocyclic ring starting material compounds, such as 1-methylpyrroline or 3-methylpyrrole.

However, further in connection with aromatic rings that are heterocyclic, it has been found that the starting material compound may not be 4-methylpyridine (also known as gamma-picoline). More particularly, attempts to employ the method of the present invention for oxidation of the pendent methyl moiety into the aldehyde moiety for this 6-member heterocyclic ring starting material compound produced either no product at all or only trace amounts of 4-pyridine-aldehyde. While it is not intended to be bound to any theory, it is believed that the reason involves electron deficiency in that the N in the ring for 4-methylpyridine has a free electron pair but no H attached to it, whereas the N in the ring for each of 1-methylpyrroline and 3-methylpyrrole is attached to an H.

In addition to having a pendent methyl moiety, the aromatic ring may be substituted with various other moieties, generally designated as one or more of R, on condition that, as noted above, at least one of the two positions ortho to the carbon having the methyl moiety is unsubstituted. When there are more than one R, they may be the same or different.

Pendant R may be alkyl of 2 or more carbons, for instance, ethyl, propyl, butyl, pentyl, hexyl, heptyl, octyl, nonyl, decyl and the like. Also, R may be alkoxy, for instance methoxy, ethoxy, propoxy, butoxy, pentoxy, hexoxy, hepoxy, octoxy, nonoxy, decoxy and the like. Additionally, R may be nitro, phosphoro, and the like. It is further noted that R may be halo, such as fluoro, chloro, bromo, or iodo.

Also, other rings may be present together with the aromatic ring having a pendent methyl moiety. For instance, the starting compound may be methyl-substituted naphthalene, methyl-substituted quinoline, and the like.

Preferred starting material aromatic compounds having a pendent methyl moiety are 6-member homocyclic ring compounds including, but not limited to, toluene and substituted toluene, such as p-nitrotoluene, m-chlorotoluene, or 3,4-dimethoxytoluene.

The enzymatic catalyst comprises an electron transferase. The most preferred electron transferase is laccase, a blue-colored metalloglycoprotein containing four copper ions in the active sites. Laccase is also known as benzenediol:oxygen oxidoreductase; EC 1.10.3.10.

As reported by Moroshi et al. in *Mokuzai Gakkaisha*, Vol. 33, pp. 218–215 (1987), laccase has been intensively investigated due to its ability to degrade bipolymeric structures. Also, it has been intensively investigated due to its usefulness in the synthesis of organic compounds, as reported by Potthast, Rosenau, Chen, and Gratzl in "A Mild, Simple and General Procedure for the Oxidation of Benzyl Alcohols to Benzaldehydes", Vol. 26, No. 2, *Synthetic Communications*, pp. 315–320 (February, 1996). The laccase may be obtained from *Coriolus versicolor*, or other micro-organisms that produce laccase.

It is well known to those skilled in the art that laccase, by itself, reacts with phenolic and anilinic substrates. Thus, if the above-noted R on the aromatic ring is a hydroxyl pendent moiety or an amino pendent moiety, these groups will require protection, as it is known that laccase reacts with phenols and anilines under a hydrogen atmosphere, leaving behind radicals that may undergo coupling or other reactions.

For the method of the present invention, the laccase must be applied together with a mediator to cause the pendent methyl moiety to be oxidized to the pendent formaldehyde moiety. The most preferred mediator is the diammonium salt of 2,2'-azinobis (3-ethylbenzothiazoline-6-sulfonic acid), which is abbreviated in the Laboratory Examples as ABTS-$(NH_4)_2$. Other suitable mediators include, but are not limited to, 1-hydroxybenzotriazole.

While it is not intended to be bound to any theory, it is believed that the mediator functions as a single-electron donor and activator of the laccase, but that the mediator does not act as an oxidant of the aromatic compound having a pendent methyl moiety. Discussions of various mediators for laccase can be seen in Solomon et al., "Electronic Structures of Active Sites in Copper Proteins: Contributions to Reactivity", Vol. 92, *Chemical Review*, pp. 521–542 (1992); Solomon et al., "Electronic Structure Contributions to Function in Bioinorganic Chemistry", Vol. 259, *Science, pp.* 1575–1581 (Mar. 12, 1993); International Publication No. WO 92/20867, published Nov. 26, 1992 (based on International Application No. PCT/EP92/01086 to Call); Bourbonnais et al., "Oxidation of Non-Phenolic Substrates—An Expanded Role for Laccase in Lignin Biodegradation", Vol. 267, No. 1, *Federation of European Biochemical Societies Letters*, pp. 99–102 (1990); and Wong et al., "Enzymes in Organic Synthesis: Application to the Problems of Carbohydrate Recognition (Part 1)", Vol. 34, *Angew. Chem. Int. Ed. Engl.,* pp. 412–432 (1995).

The reaction of converting the pendent methyl moiety on the aromatic ring into the corresponding pendent aldehyde moiety should be carried out in the presence of oxygen. Thus, the reaction may be performed solely in the ambient air, but it is preferred to carry out the reaction with intermittent oxygen flushing. While it is not intended to be bound to any theory, it is believed that the oxygen flushing should be performed in order to facilitate the laccase in accomplishing the four-electron transfer from the aromatic compound to the molecular oxygen, which is then reduced to water.

Moreover, the reaction of converting the pendent methyl moiety on the aromatic ring into the corresponding pendent formaldehyde moiety proceeds under relatively mild conditions of pressure and temperature. More particularly, the reaction may be carried out at ambient pressure, for instance, atmospheric pressure of about 760 mm, but the pressure may range from about 740 mm to about 780 mm. Also, the reaction may be carried out at ambient temperature, for instance, room temperature of about 22° C. to about 23° C., but the temperature may range from about 20° C. to about 40° C.

The pH of the reaction should be acidic, preferably from about 4.0 to about 6.0, and pH=4.5 is most preferred.

The reaction time will increase with increasing quantities of reactants, but, in general, is less than the time for the above-noted selective oxidation to aldehydes employing benzeneseleninic acid as reported by Barton et al., supra.

Yields of the benzaldehyde compound are about 89% and higher, as high as about 98%, as can be seen in the Laboratory Examples below.

The following experiments were performed.

LABORATORY EXAMPLES

Selected aromatic compounds having a pendent methyl moiety were employed as starting materials. The ABTS-$(NH_4)_2$ mediator was purchased from Aldrich, Milwaukee, Wis. The enzymatic catalyst was laccase from *Coriolus versicolor* and was purchased from Mercian Corporation, Tokyo, Japan, as a suspension in 0.1M sodium phosphate buffer with pH=6. The laccase had an enzymatic activity of 51 Units/ml, as determined using the p-hydroxymandelic acid assay method reported by Agematu et al., Vol. 57, *S. Biosci. Biotech. Biochem.*, p. 1877 (1993).

The procedures were performed at ambient conditions of temperature and pressure, unless otherwise indicated below.

For each reaction, a 250 ml flask was equipped with a magnetic stirrer. Placed in the flask was 0.1 mmol (0.0548 g) of ABTS-$(NH_4)_2$ in 30 to 50 ml of acetate buffer (pH=4.5). Then, an aqueous solution containing 10 to 20 mmol of the particular aromatic compound starting material was added to the flask with vigorous stirring.

In the event the particular aromatic compound starting material had limited water solubility or was water insoluble, the starting material was instead dissolved in 20 ml of freshly distilled tetrahydrofuran or dioxane, and then the resultant solution added to the ABTS-$(NH_4)_2$ in acetate buffer. After addition, more tetrahydrofuran or dioxane was added until all the starting material had dissolved.

Then, 0.1 ml of laccase suspension was added to the flask. The flask was flushed with $O_2$ for 1 minute, closed and continuously shaken. Each reaction was carried out with flushing of the reaction mixture with oxygen. It is noted that di-oxygen (i.e., molecular oxygen) was preferred, rather than flushing of the reaction mixture with air or with atomic oxygen.

After addition of the laccase, the colorless solution immediately turned to a deep blue-green color.

The course of each reaction was monitored by means of gas chromatography or by a combination of gas chromatography with mass spectroscopy, using p-methoxyacetophenone as an internal standard. The gas chromatograph was Hewlett Packard Model 5890 Series II with a capillary column (DB-5, 30 m length×0.32 mm internal diameter) and the combination gas chromatograph with mass spectroscopy was Hewlett-Packard Model 5985B, EI mode, 70 ev. Low attenuation was used to ensure than no by-product in small amounts remained undetected.

For each reaction, the mixture was vigorously stirred at room temperature until the deep blue-green color faded. When the initial blue color of the laccase disappeared, a 0.5 ml aliquot was taken of the reaction mixture. The aliquot was extracted with $CH_2Cl_2$, and the resultant analyzed by gas chromatography or by the combination gas chromatography/mass spectroscopy for the presence of the corresponding aldehyde and to determine if some of the aromatic compound starting material was still present.

If, at this point, not all of the aromatic compound starting material was converted to the corresponding aldehyde, an additional 0.3 ml of laccase solution and 0.01 mmol (0.0055 g) of ABTS-$(NH_4)_2$ were added. Analysis of 0.5 ml aliquots by gas chromatography or by the combination gas chromatography/mass spectroscopy was repeated at selected intervals until the presence of the aromatic compound starting material could not be detected, usually about 12 hours at room temperature. In the early stages of each reaction and in the case of an insufficient amount of the laccase catalyst being present, the corresponding benzyl alcohol was detected in addition to the desired corresponding aromatic aldehyde.

The reaction mixture was kept at 40° C. for an additional 24 hours, and during this time, flushed with $O_2$ for 1 minute every 8 hours for a total of 3 flushings. After cooling to room temperature, the reaction mixture was extracted 3 times with $CH_2Cl_2$ and the aqueous layer was discarded. The organic phase was dried over $MgSO_4$ and the solvent slowly removed under reduced pressure. The corresponding aldehyde obtained did not require further purification in most cases.

The results are summarized in the Table 1 below.

TABLE 1

| Toluene (or toluene derivative) starting material | Corresponding aldehyde product obtained | Yield (%) |
| --- | --- | --- |
| toluene | benzaldehyde | 92 |
| p-nitrotoluene | p-nitrobenzaldehyde | 98 |
| m-chlorotoluene | m-chlorobenzaldehyde | 89 |
| 3,4-dimethoxytoluene | 3,4-dimethoxy-benzaldehyde | 90 |

It will be understood that various details of the invention may be changed without departing from the scope of the invention. Furthermore, the foregoing description is for the purpose of illustration only, and not for the purpose of limitation—the invention being defined by the claims.

What is claimed is:

1. A method for manufacturing a corresponding aromatic aldehyde compound from an aromatic compound, the method comprising:

(A) providing (i) an aromatic compound, having a pendent methyl moiety substituted on at least one carbon of the aromatic compound with at least one unsubstituted position ortho to the carbon substituted with the pendent methyl moiety, for catalytic conversion into the corresponding aromatic aldehyde compound, (ii) a mediator, and (iii) a laccase, wherein the aromatic compound and the mediator are present in a mmol ratio of the aromatic compound to the mediator of about 1000:5 to about 1000:11, and a sufficient amount of the laccase is present to provide about 25 to about 210 Units of enzymatic activity;

(B) reacting the aromatic compound, the mediator, and the laccase of step (A) in the presence of oxygen at a temperature from about 20° C. to about 40° C. and a pressure from about 740 mm to about 780 mm and a pH from about 4.0 to about 6.0; and (C) obtaining the corresponding aromatic aldehyde.

2. The method of claim 1, wherein the aromatic compound includes at least one aromatic ring substituted with at least one pendent methyl moiety, wherein said one aromatic ring is selected from the group consisting of 5-member, 6-member, and 7-member aromatic rings.

3. The method of claim 2, wherein the 5-member, 6-member, and 7-member aromatic rings are selected from the group consisting of homocyclic rings and heterocyclic rings.

4. The method of claim 1, wherein the aromatic compound is selected from the group consisting of toluene, p-nitrotoluene, m-chlorotoluene, and 3,4-dimethoxytoluene.

5. The method of claim 1, wherein the laccase is obtained from *Coriolus versicolor*.

6. The method of claim 1, wherein the aromatic aldehyde is selected from the group consisting of benzaldehyde, p-nitrobenzaldehyde, m-chlorobenzaldehyde, and 3,4-dimethoxybenzaldehyde.

7. The method of claim 1, wherein step (B) further includes intermittent flushing with pure oxygen.

8. The method of claim 1, wherein the aromatic aldehyde in step (C) is obtained in a yield from about 89% to about 98%.

9. The method of claim 1, wherein the mediator is selected from the group consisting of 2,2'-azinobis(3-ethylbenzothiazoline-6-sulfonic acid) diammonium salt; 1-hydroxybenzotriazole; and combinations thereof.

* * * * *